United States Patent [19]

Richard et al.

[11] Patent Number: 4,684,483
[45] Date of Patent: Aug. 4, 1987

[54] PREPARATION OF N-SUBSTITUTED AMINO ACIDS

[75] Inventors: Thomas J. Richard, University City; William H. Miller, Glendale, both of Mo.

[73] Assignee: Monsanto Company, St. Louis, Mo.

[21] Appl. No.: 778,840

[22] Filed: Sep. 23, 1985

[51] Int. Cl.$^4$ .................................................. C07F 9/36
[52] U.S. Cl. ............................ 260/502.5 F; 562/556; 562/564; 562/567; 562/571; 562/574; 562/575
[58] Field of Search ................. 260/502.5 F; 562/571, 562/575, 567, 556, 574, 564

[56] References Cited

U.S. PATENT DOCUMENTS

| 2,164,781 | 7/1939 | Platz et al. | 562/575 |
| 3,835,000 | 9/1974 | Frazier et al. | 204/78 |
| 3,927,080 | 12/1975 | Gaertner | 260/502.5 |
| 3,956,370 | 5/1976 | Parry et al. | 260/502.5 F |
| 3,969,398 | 7/1976 | Hershman | 260/502.5 |
| 4,073,804 | 2/1978 | Hearon et al. | 562/575 |
| 4,094,928 | 6/1978 | Gaertner | 260/502.5 F |
| 4,369,142 | 6/1983 | Moser | 260/502.5 |
| 4,442,041 | 4/1984 | Subrámanian | 260/502.5 F |
| 4,486,358 | 12/1984 | Moser | 260/502.5 |

FOREIGN PATENT DOCUMENTS 0055695 7/1982 European Pat. Off. .
0156449 9/1982 Japan .................................. 502/575

OTHER PUBLICATIONS

Maurer & Woltersdorf, "Formation of Amino Acids from α-Dicarbonyl Compounds", Z. Physiol. Chem., 254, 18–24 (1938).

Primary Examiner—J. E. Evans
Attorney, Agent, or Firm—Frank D. Shearin

[57] ABSTRACT

An N-substituted amino acids can be prepared by the steps of: bringing together under reaction condition glyoxal and a source of sulfur dioxide in an aqueous medium to produce a sulfonated intermediate; and introducing into said medium a nitrogen compound selected from the group consisting of ammonia, a primary amine, and a secondary amine, into said medium containing said intermediate to produce said N-substituted amino acid.

3 Claims, No Drawings

PREPARATION OF N-SUBSTITUTED AMINO ACIDS

BACKGROUND OF THE INVENTION

This invention relates to the field of the synthesis of amino acids and, more particularly, to the synthesis of N-substituted amino acids by the reaction of glyoxal with a source of sulfur dioxide and either a primary amine, a secondary amine, or ammonia.

The N-substituted alpha-amino acids provided by the process of this invention have a number of important and varied uses. Some of these compounds can be employed as buffering agents in pharmaceutical and cosmetic preparations. Also, many can be employed as key intermediates in the manufacture of peptides, plastics, polymers, and herbicides. Exemplary of an intermediate employed in the production of a herbicide is the preparation of N-phosphonomethylglycine through N-benzylglycine as described in U.S. Pat. No. 3,835,000. The copending and coassigned application of Miller, et al., Ser. No. 687,404 filed Dec. 28, 1984, now abandoned, describes the preparation of N-phosphonomethyglycine salts by the dealkylation of N-alkyl-N-phosphonomethylglycine under alkaline conditions.

Because of its commercial importance, many processes for making glyphosate have been published. One conventional process for the manufacture of glyphosate is described by Hershman in U.S. Pat. No. 3,969,398. In that process, iminodiacetic acid is reacted with formaldehyde and phosphorous acid to produce an intermediate N-phosphonomethyliminodiacetic acid. This intermediate is oxidized to produce glyphosate.

Another process for the manufacture of glyphosate is described by Gaertner in U.S. Pat. No. 3,927,080. Gaertner describes the production of glyphosate wherein N-t-butyl-N-phosphonomethylglycine or its esters are hydrolyzed under acidic conditions. In the process of Gaertner, t-butylamine is reacted with a bromoacetate ester to produce an ester of N-t-butylglycine, which is in turn reacted with formaldehyde and phosphorous acid to produce the N-t-butyl-N-phosphonomethylglycine intermediate.

European Pat. No. 0,055,695 discloses a process for splitting off a substituent group from the nitrogen atom of an N-substituted N-phosphonomethylglycine by hydrogenolysis. The N-substituent is described as a 1-arylalkyl group suitable for hydrogenolytic cleavage. The hydrogenolytic process is carried out in the presence of a catalyst such as platinum or palladium on barium sulfate.

It may be noted that the various N-substituted amino acids play a prominent role in the processes which are available to the art for the manufacture of glyphosate. Thus, for example, the Hershman patent utilizes an iminodiacid directly in the synthesis of glyphosate, and the N-substituted glyphosates used in the synthesis schemes of Gaertner, European Pat. No. 0,055,695 can be prepared by phosphonomethylation of N-alkyl amino acids. Accordingly, there is a substantial need for economical methods for the preparation of N-substituted amino acids.

Moser U.S. Pat. Nos. 4,369,142 and 4,486,358 describes a method for the direct preparation of glyphosate by reacting aminomethylphosphonic acid with glyoxal, in an aqueous medium and in the presence of sulfur dioxide gas. In the method described by Moser, a suspension of aminomethylphosphonic acid and glyoxal is initially prepared, after which sulfur dioxide is introduced into the suspension at 10° to 15° C. with vigorous stirring and cooling. Further cooling causes the glyphosate product to precipitate, after which it is recovered by filtration. In an alternative reaction scheme, a suspension of glyoxal-bis-(sodium hydrogen sulfite) and aminomethylphosphonic acid is refluxed with stirring. The glyphosate product is recovered by a series of acidification, evaporation, and crystallization steps.

Maurer and Woltersdorf, "Formation of amino acids from α-dicarbonyl compounds. Glycine derivatives from Glyoxal," Z. Physiol. Chem., 254, 18–24 (1938) describe the preparation of amino acid amides by heating glyoxal bisulfite in solution with aliphatic amines. Examples include the preparation of N,N-diethylglycinediethylamide, N-ethylglycineethylamide-HCl, and sarcosinemethylamide-HCl. The reference further reports production of the ethyl ester of N,N-diethylglycinate by heating diethylamine in ethyl alcohol with polymeric glyoxal, and distillation of the product.

SUMMARY OF THE INVENTION

Among the several objects of the present invention may be noted the provision of a novel process for the preparation of N-substituted amino acids; the provision of a process for the preparation of amino acids which are N-substituted with alkyl and substituted alkyl groups; the provision of a process for the preparation of N-substituted amino acids in satisfactory yields; the provision of such a process which can be implemented at relatively low capital cost; the provision of a process adaptable to the preparation of either iminodiacids, such as iminodiacetic acid, or N-alkylglycine.

These and other objects are achieved by a novel process for the preparation of an N-substituted amino acid, which comprises bringing together under reaction conditions glyoxal, in a medium comprising a polar solvent, with a source of sulfur dioxide and a nitrogen compound represented by the formula:

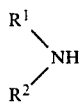

where $R^1$ and $R^2$ are independently selected from the group consisting of hydrogen, alkyl, hydroxyalkyl, alkoxyalkyl, mercaptoalkyl, alkylthioalkyl, carboxyalkyl, haloalkyl, nitroalkyl whereby there is produced an N-substituted amino acid represented by the formula:

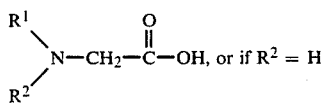

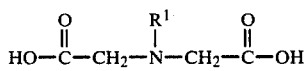

where $R^1$ and $R^2$ are as defined above.

The invention is further directed to a novel process for the preparation of an N-substituted amino acid in which glyoxal is brought together under reaction conditions with a source of sulfur dioxide in a medium comprising a polar solvent to produce a sulfonated intermediate. A nitrogen compound selected from among ammonia, a primary amine, and a secondary amine is introduced into the polar solvent medium to produce the N-substituted amino acid.

Other objects and features will be in part apparent and in part pointed out hereinafter.

DESCRIPTION OF THE PREFERRED EMBODIMENTS

In accordance with the present invention, it has been discovered that N-substituted amino acids can be produced in reasonably high, economically viable, yields by bringing together glyoxal in an aqueous medium with a source of sulfur dioxide and a primary or secondary amine. The process can also be carried out with ammonia, forming if desired, iminodiacetic acid using two equivalents of glyoxal. Although an aqueous medium is strongly preferred, it is possible to carry out the process in a medium which comprises another polar solvent, such as, for example, a low molecular weight ($C_1$ to $C_8$) alcohol or dimethylsulfoxide.

Where the nitrogen compound is an amine, it may comprise a variety of alkyl or substituted alkyl substituents. Thus, the amine reactant generally corresponds to the formula:

where $R^1$ and $R^2$ are independently selected from among: hydrogen; unsubstituted alkyl such as, for example, methyl, ethyl, propyl, n-pentyl, isopropyl, n-butyl, isobutyl, t-butyl, n-hexyl, n-octyl, and 2-ethylhexyl; hydroxyalkyl, such as hydroxyethyl, 4-hydroxyhexyl, and 6-hydroxy-2-ethylhexyl; alkoxyalkyl, such as 3-ethoxypropyl, 6-propoxy-2-ethylhexyl, and 10-methoxydecyl; mercaptoalkyl such mercaptoethyl, and 4-mercaptobutyl; alkylthioalkyl, such as methylthiomethyl, 3-methylthiopropyl, 6-ethylthio-2-ethylhexyl, and 4-propylthiohexyl; carboxyalkyl, such as carboxymethyl, 2-carboxyethyl, 5-carboxypentyl; haloalkyl, such as chloroethyl, 3-bromopropyl, 6-chloro-2-ethylhexyl, and 4-iodobutyl; nitroalkyl, such as nitromethyl, nitroethyl, 4-nitrobutyl, and 6-nitrooctyl.

Preferably, the process of the invention is carried out using either a primary amine or ammonia as the nitrogen compound reactant. Secondary amines can also be used but react somewhat more sluggishly, and do not generally provide yields as high as those achieved with primary amines or ammonia. For preparation of monobasic N-substituted amino acids (N-substituted glycines), it is generally preferred that the substituent on the primary amine be an unsubstituted alkyl. Thus, for example, the process may be advantageously carried out using a primary amine such as methylamine, ethylamine, propylamine, isopropylamine, n-butylamine, sec-butylamine, n-pentylamine, t-butylamine, n-hexylamine, n-octylamine, or 2-ethylhexylamine. It has been found that the yields tend to decline as the chain length of the alkyl substituent increases, apparently because the hydrophobicity of the amine increases with alkyl chain length. Thus, the process of the invention is particularly advantageous for the preparation of monobasic amino acids having relatively low molecular weight alkyl groups substituted on the amino nitrogen.

As noted above, however, the process of the invention is also effective for the preparation of iminodiacids such as iminodiacetic acid. The latter product may be produced either by using one equivalent of glyoxal with one equivalent of glycine, or by using two equivalents of glyoxal with one equivalent of ammonia or a primary amine to provide a product represented by the formula:

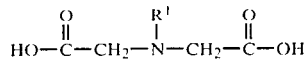

where $R^1$ is as defined above. Other iminodiacids can by produced by reaction of other amino acids with a single equivalent of glyoxal. Generally, therefore, the product of the reaction corresponds to the formula:

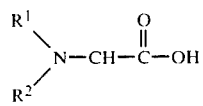

where $R^1$ and $R^2$ are as defined above.

In carrying out the process of the invention, it is preferred that the source of sulfur dioxide be first added to an aqueous solution of glyoxal to form a sulfonated intermediate. Thereafter, the nitrogen compound is added to the aqueous medium containing the sulfonated intermediate to produce the N-substituted amino acid product. It is also possible to carry out the process by first mixing the nitrogen compound with glyoxal in the aqueous reaction medium, and then adding the source of sulfur dioxide. However, it has been discovered that significantly improved yields are realized if the reactants are introduced in the preferred sequence, as described above.

Conveniently, sulfur dioxide may be supplied by bubbling gaseous $SO_2$ into the aqueous or other polar solvent medium at atmospheric pressure. However, other sources of sulfur dioxide may also be utilized. Thus, for example, the process may be carried out by addition of sulfur dioxide in the form of sulfurous acid, or in bound form such as an alkali metal bisulfite or a glyoxal/alkali metal bisulfite adduct. Preferably, at least one equivalent of sulfur dioxide source is introduced into the reaction medium per equivalent of nitrogen compound introduced. A slight excess of sulfur dioxide is preferred, but any amount greater than about two equivalents of sulfur dioxide source per equivalent of nitrogen compound does not serve any useful purpose.

It is also preferred that the number of equivalents of glyoxal initially present in the aqueous reaction medium exceed the number of equivalents of nitrogen compound introduced into the medium. More preferable, the glyoxal content exceeds the amount of nitrogen compound introduced by at least about 30%. The initial concentration of glyoxal in the aqueous or other polar solvent medium should be at least about 10% by weight. To maximize payload, the initial concentration of glyoxal is preferably greater than 25% by weight, most preferably about 40% by weight. Preparatory to the introduction of other reactants, the aqueous medium containing glyoxal is preferably cooled to room temperature, most preferably 0°–5° C. Thereafter, the other reactants are slowly added to the medium, preferably in the sequence discussed above. Once both the source of sulfur dioxide and the nitrogen compound have been added, the reaction medium is slowly heated to a temperature of between about 65° and about 100° C., preferably between about 80° and 90° C., and maintained within such range until the product has been formed. Higher temperatures may be used, but temperatures significantly above 100° C. would require that the system be maintained under pressure.

The product N-substituted amino acids may be isolated, if desired, using conventional methods of separation, such as, for example, ion exchange chromatography. In some instances, it may be feasible to recover the product by crystallization. As a further alternative, the product of the reaction may not be isolated, but the reaction solution instead used directly in the synthesis of further products. Thus, for example, an N-alkylamino acid reaction product can be further reacted with formaldehyde and phosphorous acid to produce an N-alkyl-N-phosphonomethylamino acid, such as N-alkyl-N-phosphohomethylglycine, which can in turn be dealkylated under alkaline conditions to the N-phosphonomethylamino acid using the method of the co-pending and coassigned applications of Pulwer, et al., Ser. No. 687,313 filed Dec. 28, 1984 and Miller, et al., Ser. No. 687,404 also filed Dec. 28, 1984. In connection with the latter process, it is particularly preferred that the process of this invention be employed to produce N-isopropylglycine using glyoxal with a source of sulfur dioxide and isopropylamine.

The process of the present invention is straightforward to operate and is subject to implementation in conventional process equipment. The process can be carried out using a single process vessel, and substantial reactor payloads can be obtained. Commercialization of the process can be effected at relatively low capital cost.

The following examples illustrate the invention.

EXAMPLE 1

In a three-neck round bottom flask equipped with a condenser, a thermometer, a gas inlet tube, and a stir bar was added 9.58 g (0.065 mol) of a 40% by weight aqueous solution of glyoxal and water (40 ml). The solution was stirred and cooled to 0°-5° C. and 3.20 g (0.05 mol) of sulfur dioxide was slowly bubbled into the reaction mixture. While continuing cooling, 2.96 g (0.05 mol) of isopropylamine was slowly added to the reaction mixture. The reaction mixture was then heated to 85° C. for 40 minutes. The reaction mixture was cooled and excess water was removed under reduced pressure. The residues were chromatographed on an Amberlite CG-50 ion exchange column. A total of 3.17 g (54.2% of theoretical) of N-isopropylglycine was isolated as a pale brown solid. After the solid was recrystallized from an aqueous ethanol solution, it was found to melt at 194°-197° C. Nuclear Magnetic Resonance (NMR) peaks were observed at ($D_2O$, DSS), 3.56(S,2H), 3.40 (Sept., J=7Hz, 1H), 1.31(d, J=7Hz, 6H).

EXAMPLE 2

To a three-neck round bottom flask equipped with a reflux condenser, a thermometer, a gas inlet tube and a stir bar was added a 40% by weight solution of glyoxal (18.7 g; 0.13 mol) in 40 ml water.

The solution was stirred and cooled to 0°-5° C. and sulfur dioxide (6.40 g; 0.10 mol) was thereafter bubbled slowly into the reaction mixture. While cooling was continued, isopropylamine (5.91 g; 0.10 mole) was slowly added below the surface of the reaction mixture. The reaction mixture was then heated to 85° C. for 40 minutes. Analysis by HPLC showed that N-isopropylglycine was present in 63% yield.

EXAMPLE 3

Glyoxal bis-sodium bisulfite adduct (31.2 g; 0.11 mole) and water (60 ml) were added to a three-neck-round-bottom flask that was equipped with a condenser, a thermometer and a stir bar. The resulting slurry was stirred and cooled to 0°-5° C., after which isopropylamine (5.91 g; 0.10 mole) was slowly added. The reaction mixture was then heated to 85° C. for 40 minutes, during which time all solids dissolved. Analysis by HPLC showed that N-isopropylglycine was present in a 59.0% overall yield.

EXAMPLE 4

A 40% by weight solution of glyoxal (18.7 g; 0.13 mole) and water (60 ml) was added to a three-neck round bottom flask that was equipped with a condenser, a thermometer, a gas inlet tube, and a stir bar. The solution was stirred and cooled to 0°-5° C. and sulfur dioxide (6.40 g; 0.10 mole) was slowly bubbled into the reaction mixture. While stirring and cooling was continued, glycine (7.50 g; 0.10 mole) was added to the reaction mixture. The reaction mixture was then heated to 85° C. for 45 minutes. Analysis by HPLC showed that iminodiacetic acid (IDA) was present in 63.7% yield. Upon standing, IDA began to crystallize from the reaction mixture.

EXAMPLE 5

Using the apparatus described in Example 4, a series of reactions was carried out to determine the effect of several process variables on the yields obtained in the reaction of the invention. Variables tested included the order of addition of reactants, the nature of the sulfur dioxide source, the amount of sulfur dioxide source added to the reaction mixture, and the ratio of nitrogen compound to glyoxal. In each case, reactants were added while the temperature of the contents of the reaction flask was maintained at 0°-5° C., after which the reaction mixture was heated to 85° C. and maintained at that temperature for 40 minutes. The ratios of reactants, reaction procedure, and yields obtained are summarized in Table I.

TABLE I

| PREPARATION OF N—ISOPROPYLGLYCINE FROM GLYOXAL/$SO_2$ AND ISOPROPYLAMINE* | | | | |
|---|---|---|---|---|
| Equiv. Glyoxal | Equiv. Isopropylamine | Equiv. $SO_2$ | Reaction Procedure | % Isopropylglycine by HPCL |
| 1.0 | 1.0 | excess | a | 45.5 |
| 1.0 | 1.0 | excess | b | 54.7 |
| 1.0 | 1.0 | 1.0 | c | 52.8 |
| 1.3 | 1.0 | 0.2 | d | 25.2 |
| 1.3 | 1.0 | 0.2 | g | 27.8 |
| 1.0 | 1.0 | 2.0 | e | 56.9 |
| 1.3 | 1.0 | 1.0 | d | 61.2 |
| 1.1 | 1.0 | 1.1 | f | 59.0 |
| 1.3 | 1.0 | 1.0 | b | 63.2 |
| 1.3 | 1.0 | 1.0 | d | 65.0 |
| 1.0 | 1.3 | 1.0 | b | 41.4 |
| 1.0 | 1.3 | 1.0 | b | 46.7 | a. IPA and glyoxal combined followed by addition of $SO_2$.
b. $SO_2$ bubbled into glyoxal solution followed by addition of IPA.
c. Same as b but $SO_2$ addition metered.
d. Same as in b but aqueous $HSO_3$ (6% by wt $SO_2$) used in place of gaseous $SO_2$.
e. Same as in b but $Na_2S_2O_5$ (sodium metabisulfite) used.
f. Glyoxal-bis-sodium bisulfite adduct used.
g. Reaction run in a sealed pressure bottle, procedure same as in b.
*All reactions run at 85° C. for 40 minutes with % yield based on starting amine.

EXAMPLE 6

Using the apparatus and the method of procedure "b" of Example 5, a series of reactions were conducted between glyoxal, sulfur dioxide and a variety of different amines. In each of the reactions, 1.3 moles of glyoxal and 1.0 mole of sulfur dioxide were utilized per mole of amine. The identity of the amines and yields obtained are set forth in Table II. From the results shown in Table II, it may be seen that the reaction is quite general with yields in the range of 53–65% for simple amines (i.e., $C_1$ to $C_6$). With longer chain alkylamines (e.g., $C_{12}$), the reaction still proceeds but the yields are substantially reduced, probably due to the hydrophobic nature of the amine.

As shown in Table II, secondary amines also react but in lower yields, possibly due to increased steric hindrance. Of particular interest is the fact that iminodiacetic acid (IDA) can be prepared in 63.7% yield from glycine.

TABLE II
REACTION OF GLYOXAL/SO$_2$ WITH AMINES

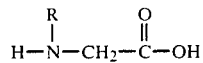

| R$^1$ | R$^2$ | % Yield |
|---|---|---|
| —CH$_2$CO$_2$H | H | 63.7 |
| —CH$_3$ | H | 54.0 |
| —(CH$_2$)$_6$— | H | 52.9 |
| CH$_2$CH$_2$OH | H | 42.1 |
| φCH$_2$ | H | 41.3 |
| CH$_3$(CH$_2$)$_{11}$ | H | 24.8 |
| (CH$_3$)$_2$CH | H | 63.2 |
| (CH$_3$)$_3$C | H | 42.0 |
| CH$_3$CH$_2$ | CH$_3$CH$_2$ | 23.2 |

EXAMPLE 7

Using the apparatus and procedure of Example 6, two runs were carried out in which glyoxal was reacted with sulfur dioxide and ammonia. In the first run, one equivalent of sulfur dioxide and one equivalent of glyoxal were charged per mole of ammonia. In the second run, two moles of glyoxal and two moles of sulfur dioxide were charged per mole of ammonia. In each run a mixture of glycine and iminodiacetic acid was produced. The results of the runs of this example are set forth in Table III.

TABLE III
PREPARATION OF IDA/GLYCINE

| Equiv. Glyoxal | Equiv. SO$_2$ | Equiv. NH$_3$ (as NH$_4$OH) | % Yield IDA | % Yield Glycine | Molar Ratio IDA/GLY |
|---|---|---|---|---|---|
| 1 | 1 | 1 | 18 | 5.8 | 1.6:1 |
| 2 | 2 | 1 | 24.9 | 5.7 | 2.96:1 |

We claim:

1. A process which comprises:
   bringing together under reaction conditions glyoxal, in a medium comprising a polar solvent, with a source of sulfur dioxide and a primary amine represented by the formula:

R—NH$_2$ where R is an alkyl group, to produce an N-substituted amino acid represented by the formula:

$$\begin{array}{c} R \quad\quad O \\ | \quad\quad\; \| \\ H-N-CH_2-C-OH \end{array}$$

contacting said N-substituted amino acid with formaldehyde and phosphorous acid in a strongly acid system under reaction conditions to produce an N-alkyl-N-phosphonomethylglycine, and
   dealkylating under alkaline conditions said N-alkyl N-phosphonomethylglycine to produce a N-phosphonomethylglycine salt.

2. A process as set forth in claim 1 wherein said primary amine is selected from the groug consisting of ethylamine, propylamine, isopropylamine, n-butylamine, sec-butylamine, n-pentylamine, n-hexylamine, n-octylamine, and 2-ethylhexylamine.

3. A process as set forth in claim 2 wherein said primary amine comprises isopropylamine.

* * * * *